United States Patent
Sugiura

(10) Patent No.: US 10,807,066 B2
(45) Date of Patent: Oct. 20, 2020

(54) ADSORBENT AND DEODORANT PROCESSED PRODUCT COMPRISING ZIRCONYL HYDROXIDE

(71) Applicant: TOAGOSEI CO., LTD., Tokyo (JP)

(72) Inventor: Koji Sugiura, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 29 days.

(21) Appl. No.: 16/342,165

(22) PCT Filed: Oct. 18, 2017

(86) PCT No.: PCT/JP2017/037659
§ 371 (c)(1),
(2) Date: Apr. 15, 2019

(87) PCT Pub. No.: WO2018/074509
PCT Pub. Date: Apr. 26, 2018

(65) Prior Publication Data
US 2019/0232250 A1 Aug. 1, 2019

(30) Foreign Application Priority Data

Oct. 18, 2016 (JP) .................................. 2016-204064

(51) Int. Cl.
| | | |
|---|---|---|
| B32B 5/16 | (2006.01) | |
| B01J 20/06 | (2006.01) | |
| A61L 9/014 | (2006.01) | |
| B01J 20/28 | (2006.01) | |
| D06M 11/46 | (2006.01) | |
| B01J 20/30 | (2006.01) | |
| B01D 53/02 | (2006.01) | |
| A61L 9/16 | (2006.01) | |
| A61L 9/01 | (2006.01) | |
| D01F 1/10 | (2006.01) | |

(52) U.S. Cl.
CPC .............. B01J 20/06 (2013.01); A61L 9/01 (2013.01); A61L 9/014 (2013.01); A61L 9/16 (2013.01); B01D 53/02 (2013.01); B01J 20/28 (2013.01); B01J 20/28004 (2013.01); B01J 20/28016 (2013.01); B01J 20/28061 (2013.01); B01J 20/3014 (2013.01); D06M 11/46 (2013.01); A61L 2209/22 (2013.01); B01D 2253/1124 (2013.01); B01D 2253/306 (2013.01); B01D 2257/90 (2013.01); B01D 2258/06 (2013.01); B01D 2259/4508 (2013.01); D01F 1/10 (2013.01)

(58) Field of Classification Search
CPC ... C01B 13/0203; C01B 13/363; C01G 25/02; C01G 27/02
USPC ........ 502/103; 423/71, 594.12, 608
See application file for complete search history.

(56) References Cited

U.S. PATENT DOCUMENTS

| | | | | |
|---|---|---|---|---|
| 2,498,514 | A * | 2/1950 | Mater ............... | A61K 8/28 424/66 |
| 5,182,408 | A * | 1/1993 | Sharif .............. | C07C 51/418 556/55 |
| 5,478,543 | A * | 12/1995 | Murota ............. | B01J 23/10 423/263 |
| 2004/0007531 | A1* | 1/2004 | Bortun ............. | B01J 21/06 210/660 |
| 2006/0110314 | A1* | 5/2006 | Torardi ............ | B82Y 30/00 423/608 |
| 2006/0110315 | A1* | 5/2006 | Torardi ............ | C01G 23/047 423/608 |

FOREIGN PATENT DOCUMENTS

| | | |
|---|---|---|
| EP | 0 629 438 A2 | 12/1994 |
| JP | 6-190274 A | 7/1994 |
| JP | 7-16452 A | 1/1995 |
| JP | 10-155884 A | 6/1998 |
| JP | 2002-200149 A | 7/2002 |
| JP | 2009-90012 A | 4/2009 |
| JP | 2012-147984 A | 8/2012 |

(Continued)

OTHER PUBLICATIONS

Pan et al., Acid and organic resistant nano-hydrated zirconium oxide (HZO)/polystyrene hybrid adsorbent for arsenic removal from water, Chemical Engineering Journal, vol. 248, Jul. 15, 2014, pp. 290-296 (Year: 2014).*

(Continued)

*Primary Examiner* — Hoa (Holly) Le
(74) *Attorney, Agent, or Firm* — Birch, Stewart, Kolasch & Birch, LLP

(57) ABSTRACT

To provide a chemical adsorbent for an acid gas, the chemical adsorbent having a high chemical adsorbing performance and not causing resin degradation, and to provide a deodorant processed product such as paper, nonwoven fabric, or fibers, the deodorant processed product exhibiting an excellent deodorizing performance by using the adsorbent.

A chemical adsorbent for an acid gas, the chemical adsorbent including an amorphous zirconyl hydroxide represented by Formula (1) below, as a main component, and a deodorant processed product in which the chemical adsorbent for an acid gas is applied or kneaded:

$$(ZrO)_{1-x}(HfO)_x(OH)_y \cdot zH_2O \qquad (1)$$

in which, in Formula (1): x, y, and z each represents a positive number; x represents a number from 0.0001 to 0.005; y represents a number from 1.9 to 3.0; and z represents a number from 0.05 to 1.0.

6 Claims, No Drawings

(56) References Cited

FOREIGN PATENT DOCUMENTS

JP              2014-54754 A        3/2014

OTHER PUBLICATIONS

Hagfeldt et al., Structure of the hydrated, hydrolysed and solvated zirconium(IV) and hafnium(IV) ions in water and aprotic oxygen donor solvents, Dalton Trans., 2004, 2142-2151. (Year: 2004).*
International Search Report for PCT/JP2017/037659 (PCT/ISA/210) dated Jan. 9, 2018.
Written Opinion of the International Searching Authority for PCT/JP2017/037659 (PCT/ISA/237) dated Jan. 9, 2018.
Extended European Search Report, dated Oct. 2, 2019, for European Application No. 17861592.8.
Kirk et al., "Vitamins To Zone Refining", Encyclopedia of Chemical Technology, Third Edition, vol. 24, pp. 864-865 and pp. 871-872 (6 pages), 1984.

* cited by examiner

ADSORBENT AND DEODORANT PROCESSED PRODUCT COMPRISING ZIRCONYL HYDROXIDE

TECHNICAL FIELD

The present invention relates to an adsorbent for an acid gas including an amorphous zirconyl hydroxide. The present invention relates to provision of a deodorant processed product such as paper, fibers, a film, or a plastic molded product, which exhibits an excellent deodorizing performance by using the adsorbent that has an excellent processability, and is less colored even if being kneaded into a resin or the like.

RELATED ART

Recently, interest in odor in daily life has been enhanced, and various deodorant processed products such as indoor standing-type and spray-type deodorant products, deodorizing wall paper, deodorizing curtain, and deodorizing clothing have been proposed for reducing unpleasant odor or bad odor. As unpleasant odor or bad odor, there has been a problem of indoor odor caused by an acid gas such as excrement odor in nursing care and animal odor of pets, so that various adsorbents have been proposed as a result of considering a deodorizing performance and safety.

Patent Document 1 discloses an acidic component adsorbent in which an alkali metal salt is allowed to be present from 2% by weight to 15% by weight in terms of an oxide in an alumina support obtained by molding a rehydrated alumina powder, subsequently subjecting the molded powder to a steam atmosphere at a room temperature to 120° C. and then calcining the resultant. Patent Document 2 discloses a deodorant for an acid malodorous gas which is made of hydrous zirconium oxide or zirconium oxide. Patent Document 3 discloses hydrous zirconium oxide as a deodorant which deodorizes bad odor caused by an acid gas such as acetic acid, isovaleric acid, and butyric acid. Patent Document 4 discloses that a deodorant containing Component (a) aluminum tripolyphosphate, Component (b) zinc oxide, Component (c) smectite, and Component (d) water has a deodorizing effect to bad odor including acetic acid or the like. Patent Document 5 discloses that a tea leaf hot water extract-sericin composite has an excellent deodorizing performance to acetic acid and the like. Also, Patent Document 6 describes interior finishing using cloth which is provided with plural deodorants, and discloses zinc oxide as a deodorant that is effective to acid gas-based smell.

PATENT DOCUMENTS

Patent Document 1: Japanese Patent Application Laid-Open (JP-A) No. H06-190274
Patent Document 2: JP-A No. H10-155884
Patent Document 3: JP-A No. 2002-200149
Patent Document 4: JP-A No. 2009-90012
Patent Document 5: JP-A No. 2012-147984
Patent Document 6: JP-A No. 2014-54754

SUMMARY OF INVENTION

Technical Problem

The above-proposed deodorant for an acid gas is an excellent adsorbent that exhibits an effect for adsorbing acid gas. However, since its adsorption capacity is insufficient, a very large addition amount of the deodorant is required to be kneaded into a resin. Further, there has been a problem of degrading a resin if a zinc compound or a strong alkali deodorant is kneaded into the resin.

Therefore, an object of the present invention is to provide a chemical adsorbent which has a high chemical adsorbing performance and does not cause resin degradation, and is to provide a deodorant processed product such as paper, nonwoven fabric, or fibers, which exhibits an excellent deodorizing performance by using the adsorbent.

Solution to Problem

The inventors of the present invention have found an excellent chemical adsorbent that exhibits a very high deodorizing performance by improving hydrous zirconyl oxide, which has been conventionally known to exhibit a deodorizing performance. Further, the inventors of the present invention have also found that paper, nonwoven fabric, fibers, plastic molded products, or the like, in which this adsorbent is applied or kneaded, cause less appearance defects such as coloration and discoloration, and exhibit a high deodorizing performance.

That is, the present invention is shown as follows.

<1> A chemical adsorbent for an acid gas, the chemical adsorbent including an amorphous zirconyl hydroxide represented by Formula (1) below, as a main component:

$$(ZrO)_{1-x}(HfO)_x(OH)_y \cdot zH_2O \qquad (1)$$

in which, in the Formula (1): x, y, and z each represents a positive number; x represents a number from 0.0001 to 0.005; y represents a number from 1.9 to 3.0; and z represents a number from 0.05 to 1.0.

<2> The chemical adsorbent for an acid gas according to <1>, in which an acetic acid gas chemical adsorption amount is 20 mL/g or more.

<3> The chemical adsorbent for an acid gas according to <1> or <2>, having a BET specific surface area of 100 m²/g or more.

<4> The chemical adsorbent for an acid gas according to any one of <1> to <3>, in which an average particle size measured by a laser diffraction particle size distribution analyzer is from 0.1 μm to 10 μm <5> A deodorant processed product, in which the chemical adsorbent for an acid gas according to any one of <1> to <4> is applied or kneaded.

Advantageous Effects of Invention

The chemical adsorbent for an acid gas of the present invention has a particularly high acid gas adsorbing performance, and hardly causes resin degradation. The adsorbent is in a form of fine particles colored in white, and thus can be applied to or kneaded into products such as paper or fibers, so that it is possible to provide a deodorant processed product such as paper, nonwoven fabric, or fibers, which exhibits an excellent deodorizing performance by using the adsorbent.

DESCRIPTION OF EMBODIMENTS

Hereinafter, the present invention will be described in detail. Incidentally, unless otherwise specified, "%" denotes "% by mass", and "part(s)" denotes "part(s) by mass".

The present invention relates a chemical adsorbent for an acid gas, the chemical adsorbent including an amorphous zirconyl hydroxide as a main component (hereinafter, also simply referred to as an "adsorbent"). The term "amorphous" means that there is no clear diffraction peak or only a slight diffraction peak due to a crystal structure in powder X-ray diffraction measurement. Amorphous powder has a large contact area with gas, and thus has excellent adsorptivity.

The term "acid gas" in the present invention means an acid gas that can cause bad odor, for example, acetic acid, isovaleric acid, and butyric acid.

The term "zirconyl hydroxide" generally means a compound represented by $ZrO(OH)_2$. Zirconium compounds have weaker catalytic activity than those of titanium compounds and zinc compounds, and thus are not likely to cause resin degradation. The zirconyl hydroxide of the present invention (the adsorbent of the present invention) has excellent acid gas adsorptivity, and thus is, in particular, an amorphous zirconyl hydroxide represented by Formula (1) below.

$$(ZrO)_{1-x}(HfO)_x(OH)_y \cdot zH_2O \quad (1)$$

In the Formula (1): x, y, and z each represents a positive number; x represents a number from 0.0001 to 0.005; y represents a number from 1.9 to 3.0; and z represents a number from 0.05 to 1.0.

A preferable range of x is from 0.0002 to 0.002, and a more preferable range thereof is from 0.0005 to 0.001. If x represents a number less than 0.0001 or more than 0.005, adsorptivity is decreased. A preferable range of y is from 2.0 to 2.9, and a more preferable range thereof is from 2.1 to 2.8. If y represents a number less than 1.9, adsorptivity becomes insufficient, and if y represents a number more than 3.0, a catalytic property is increased, whereby resin degradation may be likely to be caused. A preferable range of z is from 0.05 to 0.50, and a more preferable range thereof is from 0.07 to 0.20. If z represents a number less than 0.05, an adsorption amount is insufficient, and if z represents a number more than 1.0, foam or the like is likely to be generated during resin processing.

Incidentally, the term "main component" in the present invention means that a content of the component with respect to a total amount is 50% by mass or more, is preferably 80% by mass or more, and is more preferably 90% by mass or more. Further, an upper limit value thereof is 100% by mass.

Moreover, there is no problem if a slight amount of other component is contained in the adsorbent, since the deodorizing performance is not decreased, but the deodorizing performance is not increased significantly.

The above-described x, y, and z are values of element analysis ratios calculated from measurement results of X-ray fluorometry.

An acetic acid gas chemical adsorption capacity of the amorphous zirconyl hydroxide of the present invention is preferably 20 mL/g or more. An upper limit thereof is not particularly limited, but is preferably 200 mL/g or less, and is more preferably 100 mL/g or less.

The term "adsorption capacity" means a maximum capacity of a specific gas component that can be deodorized, absorbed or adsorbed by a compound. Incidentally, adsorption capacities are often shown when adsorption occurs through adsorption mechanisms of both physical adsorption and chemical adsorption. A method for discriminating a chemical adsorption capacity of a deodorant from a physical adsorption capacity thereof is to measure an adsorption capacity at a high adsorption test temperature. Since gas is not adsorbed at a high temperature by physical adsorption, only a chemical adsorption capacity can be discriminated to be measured at an adsorption test temperature of 40° C. or more. A specific method for measuring a chemical adsorption capacity of acetic acid gas will be described as follows.

A deodorant is put into a test bag made of a vinyl alcohol-based polymer, a polyester, or the like, which is a material that hardly adsorbs acetic acid gas and does not allow air to penetrate, and the bag is sealed. Further, acetic acid gas is injected into the sealed test bag, and the bag is subsequently stored in a thermostat at 40° C. or more. Immediately after the acetic acid gas is injected and after a certain time period of the storing, the concentration of the acetic acid gas remaining in the test bag is measured. In this measurement, a time when the remaining gas concentration after the certain time period of the storing becomes 1/10 or more of the initial gas concentration is determined as a point of breakthrough of adsorbing performance, and a difference between the remaining gas concentration at this time and the initial gas concentration is determined as an acetic acid gas amount that is adsorbed or absorbed by the adsorbent. The adsorbent having an adsorption capacity less than the above-described adsorption capacity exhibits a low adsorbing performance, so that a satisfactory deodorizing effect cannot be obtained thereby.

A BET specific surface area of the amorphous zirconyl hydroxide of the present invention is preferably 100 m²/g or more. The BET specific surface area is more preferably from 250 m²/g to 400 m²/g. If the BET specific surface area is 100 m²/g or more, a high adsorption capacity can be obtained, and if the BET specific surface area is 400 m²/g or less, manufacturing becomes easy, and problems such as aggregation caused during processing can be suppressed.

The amorphous zirconyl hydroxide of the present invention is white powder, and its powder color preferably has an L value of from 90 to 99, an a value of from −2 to 5 and a b value of from −2 to 5. If the Lab color space display is within the above-described range, the amorphous zirconyl hydroxide can be used as a deodorant for a wide variety of purposes.

An average particle size of the amorphous zirconyl hydroxide of the present invention is preferably from 0.1 μm to 10 μm and is more preferably from 0.5 μm to 3 μm. If the average particle size is 0.1 μm or more, aggregation can be suppressed and processability can be excellent, and if the average particle size is 10 μm or less, processing into fine fibers, a thin film, or the like can be easier, and outer appearance of a molded product can be better. Further, a maximum particle size of the amorphous zirconyl hydroxide of the present invention is preferably 20 μm or less, and is more preferably 5 μm or less. If the maximum particle size is 20 μm or less, processing can be easier, and outer appearance of a molded product can be better.

The above-described average particle denotes a value of particle size D50 obtained by measuring particle sizes by a laser diffraction particle size distribution analyzer, and analyzing a result in terms of a volume.

To a method for producing the amorphous zirconyl hydroxide of the present invention, a conventional technique can be adopted, and there is no limitation on raw materials, production methods, facilities, and the like. An outline of the production method will be described as follows.

The zirconyl hydroxide of the present invention can be obtained by a first process of dissolving, for example, a soluble zirconium salt and a soluble hafnium salt into water to prepare an aqueous solution, a second process of adding a base into the aqueous solution to produce a hydroxide, and a third process of separating and collecting the hydroxide.

The soluble zirconium salt to be used in the first process is not particularly limited as long as it is soluble into water, and a soluble zirconium salt that can be obtained by a known production method or a commercially available product can be also used. For example, a nitrate such as zirconium oxynitrate, a chloride such as zirconium chloride or zirconium oxychloride, an acetate such as zirconium acetate, or the like can be used. In the present invention, among them, zirconium oxychloride is particularly preferable. A concentration of the aqueous solution of the soluble zirconium salt may be set appropriately according to solubility or the like of the soluble zirconium salt to be used, but is preferably about 10 g to about 200 g and is more preferably from 50 g to 100 g, in terms of zirconium oxide in 1 L of the aqueous solution.

The soluble hafnium salt to be used in the first process is not particularly limited as long as it is soluble into water, and a soluble hafnium salt that can be obtained by a known production method or a commercially available product can be also used. For example, a zirconium compound containing hafnium is preferable, and zirconium oxychloride containing hafnium is preferable in view of reactivity, costs, or the like. In the present invention, a content ratio of hafnium is preferably 0.2% or more and 5% or less and is more preferably 1% or more and 4% or less, with respect to zirconium, in view of the performance of the chemical adsorbent for an acid gas to be obtained.

In the first process, a hydrolytic agent may be added into the above-described aqueous solution. As the hydrolytic agent, for example, an inorganic acid such as sulfuric acid, an organic acid such as phthalic acid, an inorganic acid salt such as ammonium sulfate or aluminum sulfate, and an organic acid salt such as ammonium phthalate or sodium phthalate can be used. An addition amount of the hydrolytic agent can be changed appropriately according to the kind of the hydrolytic agent to be used, the kind of the aqueous solution to be used, or the like, but may be generally a sufficient amount to react with all of the soluble zirconium salt in the aqueous solution to form slurry, and an excessive amount of the hydrolytic agent to its stoichiometric amount may be added.

Next, in the second process, the base is added to the zirconium aqueous solution and the soluble hafnium salt to produce the hydroxide. The kind of the base to be used is not particularly limited, and for example, sodium hydroxide, potassium hydroxide, ammonia, sodium carbonate, ammonium carbonate, or the like can be used. An addition amount of the base is not particularly limited, as long as it is possible to produce the hydroxide, but is usually adjusted so that a pH of slurry, at which the hydroxide is produced by adding the base, may be preferably 9 or more, and more preferably 12.5 or more. In addition, an upper limit value of the pH is 14.

Finally, in the third process, the hydroxide produced in the second process is separated and collected. A method for separation and collection may be in accordance with a known solid-liquid separation method. For example, filtration, a centrifugal separation method, decantation, or the like can be adopted. Thereby, an amorphous zirconyl hydroxide precursor of the present invention can be obtained. After the separation and collection, the obtained amorphous zirconyl hydroxide precursor can be also washed with water, as necessary. The obtained amorphous zirconyl hydroxide precursor is required to be subject to drying treatment. A method for drying may be a known drying method, and may be either natural drying or heat drying. The amorphous zirconyl hydroxide of the present invention is subject to heat drying preferably at a temperature of from 50° C. to 150° C., and more preferably at a temperature of from 80° C. to 130° C. If the drying temperature is 150° C. or less, crystallization or the like can be suppressed and a preferable zirconyl hydroxide composition can be obtained easily. An atmosphere in the case of the heat drying is not particularly limited, but it is preferably carried out under reduced pressure in the present invention. By heat drying under reduced pressure, adsorption of carbon dioxide in the atmosphere can be prevented, and an effect of saving a drying time or the like can be obtained. After drying, the zirconyl hydroxide may be pulverized by a known method, as necessary.

Application

The amorphous zirconyl hydroxide of the present invention can be used as, in a form of powder or granules, a deodorant product contained in a case such as a cartridge, and can exhibit effect thereof while left to stand, for example, near an indoor or outdoor odor source. Further, the amorphous zirconyl hydroxide of the present invention can be blended into fibers, a paint, a sheet, a molded product or the like, as described below in detail, so that it can be utilized to manufacture a deodorant product.

One of the useful applications of the amorphous zirconyl hydroxide of the present invention is deodorant fibers. Raw material fibers in this case may be either natural fibers or synthetic fibers, and may be any of short fibers, long fibers, composite fibers having a core-sheath structure, and the like. A method for imparting a deodorizing performance to fibers by using the amorphous zirconyl hydroxide of the present invention is not particularly limited, and for example, in the case of applying the amorphous zirconyl hydroxide of the present invention to fibers by post processing, it is possible to coat surfaces of fibers with the amorphous zirconyl hydroxide by attaching a water-based or organic solvent-based suspension that contains the amorphous zirconyl hydroxide to the surfaces of the fibers by a method such as application or dipping, and subsequently removing the solvent. Also, a binder for increasing adhesion force to the surfaces of the fibers may be mixed. A pH of the water-based suspension that contains the amorphous zirconyl hydroxide is not particularly limited, but is preferably from about 6 to about 9 for exhibiting the performance of the adsorbent sufficiently.

Also, fibers provided with the deodorizing performance can be obtained by kneading the amorphous zirconyl hydroxide of the present invention into a molten resin for fibers or a solution including a dissolved resin for fibers and fiberizing it. Any known chemical fibers can be used for the resin for fibers that can be used in this method. Preferable specific examples thereof include polyester, nylon, acryl, polyethylene, polyvinyl, polyvinylidene, polyurethane, polystyrene, and the like. These resins each may be a homo-polymer or a copolymer. In the case of the copolymer, a polymerization ratio of respective copolymerization components is not particularly limited.

A ratio of the amorphous zirconyl hydroxide of the present invention to be contained in the resin for fibers is not particularly limited. Generally, if a content is increased, a stronger deodorizing performance can be exhibited and maintained for a longer period, but even if the content is increased to a certain level or more, the deodorizing effect is not changed largely or strength of the fibers may be decreased; therefore, the ratio of the amorphous zirconyl hydroxide is preferably from 0.1 parts by mass to 10 parts by mass and more preferably from 0.5 parts by mass to 5 parts by mass, with respect to 100 parts by mass of the resin for fibers. The deodorizing fibers using the amorphous zirconyl hydroxide of the present invention can be utilized in various fields that require a deodorizing performance, and can be used for many fiber products, for example, underwear, stockings, socks, futon, futon covers, seat cushions, blankets, carpets, curtains, sofas, car seats, air filters, clothes for nursing, and the like.

Other application of the amorphous zirconyl hydroxide of the present invention is a deodorizing paint. In manufacturing the deodorizing paint, oil or resin that is a main component of a paint vehicle to be used is not particularly limited, may be any of a natural vegetable oil, a natural resin, a semi-synthetic resin, and a synthetic resin, and may be either of a thermoplastic resin and a thermosetting resin. Examples of the oil and the resin that can be used include drying oil or semidrying oil such as linseed oil, Chinese tung oil and soybean oil, rosin, cellulose nitrate, ethyl cellulose, cellulose acetate butyrate, benzyl cellulose, a novolak-type or resol-type phenol resin, an alkyd resin, an amino-alkyd resin, an acrylic resin, vinyl chloride, a silicone resin, a fluoro resin, an epoxy resin, a urethane resin, a saturated polyester resin, a melamine resin, a polyvinylidene chloride resin, and the like.

The amorphous zirconyl hydroxide of the present invention can be used for either a liquid paint or a powder paint.

Further, a deodorizing paint composition using the amorphous zirconyl hydroxide of the present invention may be cured in any mechanisms, and specific examples thereof include an oxidation polymerization type, a moisture polymerization type, a thermosetting type, a catalytic curing type, an ultraviolet curing type, a polyol curing type, and the like. Moreover, pigments, dispersants, and other additives to be used in the paint composition are not particularly limited, as long as they do not have a possibility to cause chemical reaction with a fine-particle zinc oxide or a deodorant material that is used therewith. The paint composition using the adsorbent of the present invention can be prepared easily, more specifically, by sufficiently dispersing and mixing the above-described adsorbent or deodorant composition with the paint component using a general mixing equipment such as a ball mill, a roll mill, a disper, or a mixer.

A ratio of the adsorbent of the present invention to be contained in the deodorizing paint is not particularly limited. Generally, if a content is increased, a stronger deodorizing performance can be exhibited and maintained for a longer period, but even if the content is increased to a certain level or more, the deodorizing effect is not changed largely, gloss of a painted surface may be lost, or the painted surface may be broken; therefore, the ratio of the adsorbent is preferably from 0.1 parts by mass to 20 parts by mass and is more preferably from 0.5 parts by mass to 10 parts by mass, with respect to 100 parts by mass of the paint composition. The deodorizing paint in which the adsorbent of the present invention is blended can be utilized in various fields that require a deodorizing performance, and can be used for, for example, interior walls or exterior walls of buildings, cars, and trains, incineration plants, garbage disposal containers, and the like.

Further, other important application of the adsorbent of the present invention is a deodorant sheet. A material, a microstructure, or the like of a sheet material to be a raw material is not limited. A preferable material is resin, paper, or a composite thereof, and a porous material is preferable. Preferable specific examples of the sheet material include Japanese paper, synthetic paper, nonwoven fabric, a resin film, and the like, and a particularly preferable sheet material is paper including natural pulp and/or synthetic pulp. If using natural pulp, a powder of adsorbent particles is sandwiched by fibers that are branched finely, and the natural pulp has a merit of serving as a useful support without using a binder. On the other hand, synthetic pulp has a merit of excellent chemical resistance. In the case of using synthetic pulp, since it may be difficult to support an adsorbent powder by sandwiching the powder between fibers of the synthetic pulp, adhesion force between the powder and the fibers may be increased by melting a part of the fibers in the drying step after making paper, or other thermosetting resin fibers may be mixed into a part of the fibers. By using natural pulp and synthetic pulp mixed at an appropriate ratio as described above, paper having various adjusted properties can be obtained. Generally, if a ratio of synthetic pulp is higher, paper having excellent strength, water resistance, chemical resistance, oil resistance, and the like can be obtained, and on the other hand, if a ratio of natural pulp is higher, paper having excellent water absorbency, gas permeability, hydrophilicity, molding processability, texture, and the like can be obtained.

A method for supporting the adsorbent of the present invention to the sheet material is not particularly limited. The adsorbent of the present invention may be supported either during or after manufacturing the sheet, and for example, in the case of supporting the adsorbent to paper, the adsorbent may be introduced in either step during the paper making process, or a liquid in which the adsorbent is dispersed together with the binder may be applied, immersed, or sprayed to pre-manufactured paper.

Hereinafter, a method for introducing the adsorbent of the present invention during the paper making process will be described as an example. The paper making process itself may be carried out by a known method, and for example, firstly, cationic and anionic flocculants are added respectively by 5% by mass or less with respect to a total mass of slurry, which contains the adsorbent and pulp in a predetermined ratio, thereby producing an aggregate. Subsequently, paper is made from this aggregate by a known method, and is dried at a temperature of from 100° C. to 190° C., whereby the paper supporting the adsorbent can be obtained.

Since, if a support amount of an adsorbent is increased, a stronger deodorizing performance can be generally exhibited and maintained for a longer period, but even if the support amount is increased to a certain level or more, the deodorizing effect is not changed largely, a preferable support amount of the adsorbent of the present invention to the sheet material is from 0.1 parts by mass to 10 parts by mass with respect to 100 parts by mass of the sheet in the case of supporting the adsorbent or the deodorant composition to an entire of a surface and an inside of the sheet during the paper making process, and is from 0.05 $g/m^2$ to 15 $g/m^2$ in the case of supporting the adsorbent only to the surface of the sheet by post processing such as coating. A deodorant sheet using the adsorbent of the present invention can be utilized in various fields that require a deodorizing performance, and can be used for, for example, medical packaging paper, food packaging paper, electrical appliance packing paper, paper products for nursing care, freshness-retaining paper, clothing made of paper, an air cleaner filter, wall paper, tissue paper, toilet paper, and the like.

Resin Molded Product

As a use of the adsorbent of the present invention, application to a resin molded product can be exemplified. In the case of adding the adsorbent of the present invention to resin, it is possible to mix the resin and the adsorbent directly and put them into a molding machine to mold them, or prepare pellet resin that contains a high concentration of the adsorbent in advance, and mix the pellet resin with main resin and then mold them. Further, various other additives such as a pigment, a dye, an antioxidant, a photoresistant stabilizer, an antistatic agent, a foaming agent, an impact resistance reinforcing agent, glass fibers, a desiccant, or an extender can be also blended as necessary into the resin for improving the properties. As a molding method for manufacturing a deodorant resin molded product using the adsorbent of the present invention, general resin molding methods such as injection molding, extrusion molding, inflation molding, and vacuum molding can be adopted. The deodorant resin molded product using the adsorbent or the deodorant composition of the present invention can be utilized in various fields that require a deodorizing performance, and can be used for, for example, home electric appliances such as an air cleaner and a refrigerator, general domestic utensils such as a trash can and a drainer, various nursing care equipment such as a portable toilet, daily necessaries, and the like.

EXAMPLES

Hereinafter, the present invention will be described more specifically by way of examples, but is not limited to these examples. Incidentally, "%" denotes "% by mass". Powder properties and a deodorizing performance of the adsorbent of the present invention were measured by following methods.

(1) Powder Crystallinity

Powder crystallinity was evaluated from an x-ray diffraction image obtained with Cu-Kα rays using an X-ray diffractometer "RINT2400V" (model name) manufactured by Rigaku Corporation. Measurement conditions were a tube voltage of 40 kV and a current of 150 mA. If a clear diffraction peak was observed, the adsorbent was judged to be crystalline, and if not observed, it was judged to be amorphous.

(2) Element Composition

Measurement of X-ray fluorometry was carried out using a ZSX100e-type X-ray fluorometer manufactured by Rigaku Corporation, and the obtained result was analyzed in terms of an amount of substance to calculate an element composition (molar) ratio.

(3) Particle Size D50

A particle size D50 of the adsorbent was measured by a laser diffraction particle size distribution analyzer, and the obtained result was analyzed in terms of volume. Incidentally, although a content ratio (%) in the particle size distribution denotes "% by volume" with respect to the total particles from this analysis method, since density of the measured powder is constant, the content ratio (%) means "% by mass". Specifically, the particle size D50 was measured by a laser diffraction particle size distribution measurement device "MS2000" manufactured by Malvern Panalytical Ltd.

(4) BET Specific Surface Area

A BET specific surface area was measured using a continuous-flow surface area analyzer "SA-6200" manufactured by HORIBA, Ltd. according to "Determination of the Specific Surface Area of Powders (Solids) by Gas Adsorption Methods" in JIS Z8830:2001.

(5) Acetic Acid Gas Chemical Adsorption Capacity of Powder 0.01 g of a dried adsorbent powder was put into a test bag made of a vinyl alcohol-based polymer film, 3 L of an acetic acid gas (initial concentration of 100 ppm) was injected thereto, and a concentration of the gas remaining in the Tedlar bag after 30 minutes was measured by a gas-detecting tube.

(6) Deodorizing Performance of Deodorant Processed Product

A deodorant processed product having an area of 100 $cm^2$ was put into a test bag made of a vinyl alcohol-based polymer film, 3 L of an acetic acid gas (initial concentration of 30 ppm) or an ammonia gas (initial concentration of 100 ppm) was injected thereto, and a concentration of the gas remaining in the test bag after 2 hours was measured by a gas-detecting tube

Example 1

While stirring 5% aqueous solution of zirconium-hafnium oxychloride, 5% aqueous solution of sodium hydroxide was gradually added thereto to adjust pH of the mixture to 13, thereby preparing slurry of white precipitates.

The obtained slurry was filtered, was washed with water, and was thereafter dried at 100° C. By pulverizing the dried white powder, an amorphous zirconyl hydroxide powder was obtained. A composition, a particle size D50, a specific surface area and an acetic acid deodorizing capacity of the powder of the obtained amorphous zirconyl hydroxide were measured, and results are shown in Table 1.

Example 2

The same operations, analyses, and the like as those of Example 1 were carried out except for adjusting the pH of the mixture to 11, and results are shown in Table 1.

Example 3

The same operations, analyses, and the like as those of Example 1 were carried out except for adjusting the pH of the mixture to 9, and results are shown in Table 1.

Example 4

The same operations, analyses, and the like as those of Example 1 were carried out except for drying the slurry at 130° C., and results are shown in Table 1.

Comparative Example 1

The same operations, analyses, and the like as those of Example 1 were carried out except for adding 2% of oxalic acid, instead of the 5% aqueous solution of sodium hydroxide, to the 5% aqueous solution of zirconium-hafnium oxychloride, and drying the slurry at 250° C., and results are shown in Table 1.

Comparative Example 2

The same operations, analyses, and the like as those of Example 1 were carried out except for adding 2% of oxalic acid, instead of the 5% aqueous solution of sodium hydroxide, to the 5% aqueous solution of zirconium oxychloride, and drying the slurry at 200° C., and results are shown in Table 1.

Comparative Example 3

Commercially available zirconium hydroxide was used, and measurement results of a composition, a particle size D50, a specific surface area, and an acetic acid chemical adsorption capacity are shown in Table 1.

Comparative Example 4

Commercially available amorphous zinc oxide was used, and measurement results of a composition, a particle size D50, a specific surface area, and an acetic acid chemical adsorption capacity are shown in Table 1.

Comparative Example 5

Commercially available hydrotalcite was used, and measurement results of a composition, a particle size D50, a specific surface area, and an acetic acid chemical adsorption capacity are shown in Table 1.

TABLE 1

|  | Crystallinity | Composition | Particle Size D50 | BET Specific Surface Area ($m^2/g$) | Acetic Acid Gas Chemical Adsorption Capacity (mL/g) |
|---|---|---|---|---|---|
| Example 1 | Amorphous Zirconyl Hydroxide | $(ZrO)_{0.998}(HfO)_{0.002}(OH)_{2.7} \cdot 0.19H_2O$ | 1.3 | 334 | 34 |
| Example 2 | Amorphous Zirconyl Hydroxide | $(ZrO)_{0.998}(HfO)_{0.002}(OH)_{2.3} \cdot 0.12H_2O$ | 1.8 | 319 | 32 |
| Example 3 | Amorphous Zirconyl Hydroxide | $(ZrO)_{0.998}(HfO)_{0.002}(OH)_{2.05} \cdot 0.44H_2O$ | 2.5 | 303 | 30 |
| Example 4 | Amorphous Zirconyl Hydroxide | $(ZrO)_{0.998}(HfO)_{0.002}(OH)_{1.9} \cdot 0.11H_2O$ | 2.7 | 286 | 24 |
| Comparative Example 1 | Crystalline Zirconyl Hydroxide | $(ZrO)_{0.996}(HfO)_{0.004}(OH)_{2.3} \cdot 0.22H_2O$ | 3.0 | 231 | 17 |
| Comparative Example 2 | Crystalline Zirconyl Hydroxide | $ZrO(OH)_{2.3} \cdot 0.13H_2O$ | 6.9 | 29 | 15 |
| Comparative Example 3 | Crystalline Zirconium Hydroxide | $Zr(OH)_4 \cdot 0.4H_2O$ | 7.2 | 29 | 12 |
| Comparative Example 4 | Amorphous Zinc Oxide | $ZnO \cdot 0.3H_2O$ | 1.9 | 131 | 27 |
| Comparative Example 5 | Crystalline Hydrotalcite | $Mg_6AL_2(CO_3)(OH)_{16.4}(H_2O)$ | 7.9 | 220 | 51 |

<Evaluation 1> Deodorant-Spreading Processed Cloth

After dispersing 1 part by mass of the adsorbent of each of Examples 1 to 4 and Comparative Examples 1 to 3 as the deodorant into 100 parts by mass of water, an acrylic binder was blended into the obtained dispersion so that a binder solid content might be 1 part by mass, thereby preparing a processed liquid. A polyester cloth was immersed in this processed liquid, and was processed so that a deodorant-spreading amount after the processing might be 1 g/m², and the resultant cloth was dried at 120° C. Adsorption test using an acetic acid gas was carried out with 100 cm² of the obtained deodorant-spreading processed cloth, and results of the test are shown in Table 2.

<Evaluation 2> Deodorizing Resin Molded Product

After blending 4% of the adsorbent of each of Examples 1 to 4 and Comparative Examples 1 to 5 as the deodorant into a polyester resin MA2101 manufactured by UNITIKA LTD., an injection molding plate having a thickness of 1 mm was processed. Adsorption test using an acetic acid gas was carried out with 100 cm² of the obtained molding plate, and results of the test are shown in Table 2. Since the adsorbent of each of Comparative Examples 4 and 5 deteriorated the polyester resin too much to mold it, no plate was obtained.

TABLE 2

| | Adsorption Test Using Acetic Acid Gas ||
| | Evaluation 1 Deodorizing Cloth | Evaluation 2 Deodorizing Resin Molded Product |
|---|---|---|
| Example 1 Processed Product | >99% | 79% |
| Example 2 Processed Product | >99% | 73% |
| Example 3 Processed Product | >99% | 73% |

TABLE 2-continued

|  | Adsorption Test Using Acetic Acid Gas | |
|---|---|---|
|  | Evaluation 1 Deodorizing Cloth | Evaluation 2 Deodorizing Resin Molded Product |
| Example 4 Processed Product | >99% | 68% |
| Comparative Example 1 Processed Product | 74% | 55% |
| Comparative Example 2 Processed Product | 69% | 41% |
| Comparative Example 3 Processed Product | 29% | 34% |

<Evaluation 3> Composite Deodorant-Spreading Processed Cloth

After dispersing 0.5 parts by mass of the adsorbent of each of Examples 1 to 4 and Comparative Examples 4 to 5 as the deodorant into 100 parts by mass of water, an acrylic binder was blended into the obtained dispersion so that a binder solid content might be 0.5 parts by mass, thereby preparing a processed liquid. A polyester cloth was immersed in this processed liquid, and was processed so that a deodorant-spreading amount after the processing might be 0.5 g/m², and the resultant cloth was dried at 120° C. Similarly, after dispersing 1 part by mass of a deodorant into 100 parts by mass of water, in which the deodorant was obtained by mixing the deodorant of each of Examples 1 to 4 and Comparative Examples 4 and 5 with zirconium phosphate in a mass ratio of 1:1, an acrylic binder was blended into the obtained dispersion so that a binder solid content might be 1 part by mass, thereby preparing a processed liquid. A polyester cloth was immersed in this processed liquid, and was processed so that a deodorant-spreading amount after the processing might be 1 g/m², and the resultant cloth was dried at 120° C. Further, after dispersing 0.5 parts by mass of a deodorant made of zirconium phosphate alone into 100 parts by mass of water, an acrylic binder was blended into the obtained dispersion so that a binder solid content might be 0.5 parts by mass, thereby preparing a processed liquid. A polyester cloth was immersed in this processed liquid, and was processed so that a deodorant-spreading amount after the processing might be 1 g/m², and the resultant cloth was dried at 120° C. Adsorption test using an acetic acid gas and an ammonia gas was carried out with 100 cm² of the obtained deodorant-spreading processed cloth, and results of the test are shown in Table 3.

TABLE 3

|  | Deodorizing Test Using Acetic Acid Gas | | Deodorizing Test Using Ammonia Gas |
|---|---|---|---|
|  | Acetic Acid Gas Deodorant Alone | Mixture of Acetic Acid Gas Deodorant + Zirconium Phosphate | Mixture of Acetic Acid Gas Deodorant + Zirconium Phosphate |
| Example 1 Processed Product | >99% | >99% | >99% |
| Example 2 Processed Product | >99% | >99% | >99% |
| Example 3 Processed Product | >99% | >99% | >99% |
| Example 4 Processed Product | 95% | 96% | >99% |
| Comparative Example 4 Processed Product | >99% | 37% | 46% |
| Comparative Example 5 Processed Product | >99% | 29% | 22% |
| Zirconium Phosphate Alone | 12% | — | >99% |

The adsorbents of Examples 1 to 4 had higher acetic acid gas chemical adsorption capacities than those of the adsorbents of Comparative Examples 1 to 3, and exhibited excellent deodorizing performances with the deodorant-spreading processed cloth in the deodorizing evaluation of Evaluation 1. Also, the adsorbents of Examples 1 to 4 exhibited sufficient deodorizing performances with the deodorizing resin molded products in Evaluation 2.

It can be said that the adsorbents of Examples 1 to 4 and Comparative Examples 4 and 5 had sufficient acetic acid gas chemical adsorption capacities. However, in the deodorizing evaluation of the deodorizing resin molded products of Evaluation 2, it was not possible to knead and mold the adsorbents of Comparative Examples 4 and 5 into the polyester resin, but it was possible to knead and mold the adsorbents of Examples 1 to 4 with no problem.

Further, in the deodorizing evaluation of Evaluation 3, the adsorbents of Examples 1 to 4 blended with the basic gas deodorant exhibited a high deodorizing performance to both the acid gas and the basic gas. On the other hand, the adsorbents of Comparative Examples 4 and 5 blended with the basic gas deodorant exhibited degradation of the deodorizing effect due to antagonism, and thus had low deodorizing performances to both the acid gas and the basic gas.

INDUSTRIAL APPLICABILITY

The adsorbent of the present invention has an excellent deodorizing effect, a particularly high acid gas adsorbing performance and excellent processability. The adsorbent is in a form of fine particles colored in white, and thus can be applied to or kneaded into a product such as paper or fibers, thereby a deodorant processed product such as paper, non-woven fabric, or fibers, which exhibits an excellent deodorizing performance, can be provided by using the adsorbent.

The invention claimed is:

1. A chemical adsorbent for an acid gas, the chemical adsorbent comprising an amorphous zirconyl hydroxide represented by Formula (1) below, as a main component:

$$(ZrO)_{1-x}(HfO)_x(OH)_y \cdot zH_2O \qquad (1)$$

wherein, in Formula (1): x, y, and z each represents a positive number; x represents a number from 0.0001 to 0.005; y represents a number from 1.9 to 3.0; and z represents a number from 0.05 to 1.0.

2. The chemical adsorbent for an acid gas according to claim 1, wherein an acetic acid gas chemical adsorption amount is 20 mL/g or more.

3. The chemical adsorbent for an acid gas according to claim 1, having a BET specific surface area of 100 m²/g or more.

4. The chemical adsorbent for an acid gas according to claim 1, wherein an average particle size measured by a laser diffraction particle size distribution analyzer is from 0.1 μm to 10 μm.

5. A deodorant processed product comprising the chemical adsorbent for an acid gas according to claim 1.

6. The deodorant processed product according to claim 5, wherein the chemical adsorbent for an acid gas is applied or kneaded.

* * * * *